United States Patent [19]

Soma et al.

[11] Patent Number: 4,559,824
[45] Date of Patent: Dec. 24, 1985

[54] CERAMIC TESTING METHOD

[75] Inventors: Takao Soma; Minoru Matsui, both of Nagoya, Japan

[73] Assignee: NGK Insulators, Ltd., Japan

[21] Appl. No.: 613,534

[22] Filed: May 24, 1984

[30] Foreign Application Priority Data

Jun. 17, 1983 [JP] Japan .................................. 58-107645

[51] Int. Cl.[4] .............................................. G01J 4/02
[52] U.S. Cl. ..................................... 73/432 R; 374/5; 374/57; 501/104
[58] Field of Search ............ 73/432 Z, 432 R; 374/4, 374/5, 10, 24, 45, 46, 57; 501/104, 103

[56] References Cited

U.S. PATENT DOCUMENTS

| 3,859,106 | 1/1975 | Majumdar | 501/104 X |
| 4,018,614 | 4/1977 | Nordillie | 501/104 |
| 4,219,359 | 8/1980 | Miwa et al. | 501/104 X |
| 4,303,447 | 12/1981 | Buchanan et al. | 501/103 |

Primary Examiner—Robert Lindsay
Attorney, Agent, or Firm—Parkhurst & Oliff

[57] ABSTRACT

A method for determining an amount of non-stabilized zirconia in a ceramic specimen involves subjecting the ceramic specimen to an environment having a controlled temperature and humidity and measuring mechanical and/or chemical properties of the specimen to determine if any deterioration of the specimen has occurred.

10 Claims, 1 Drawing Figure

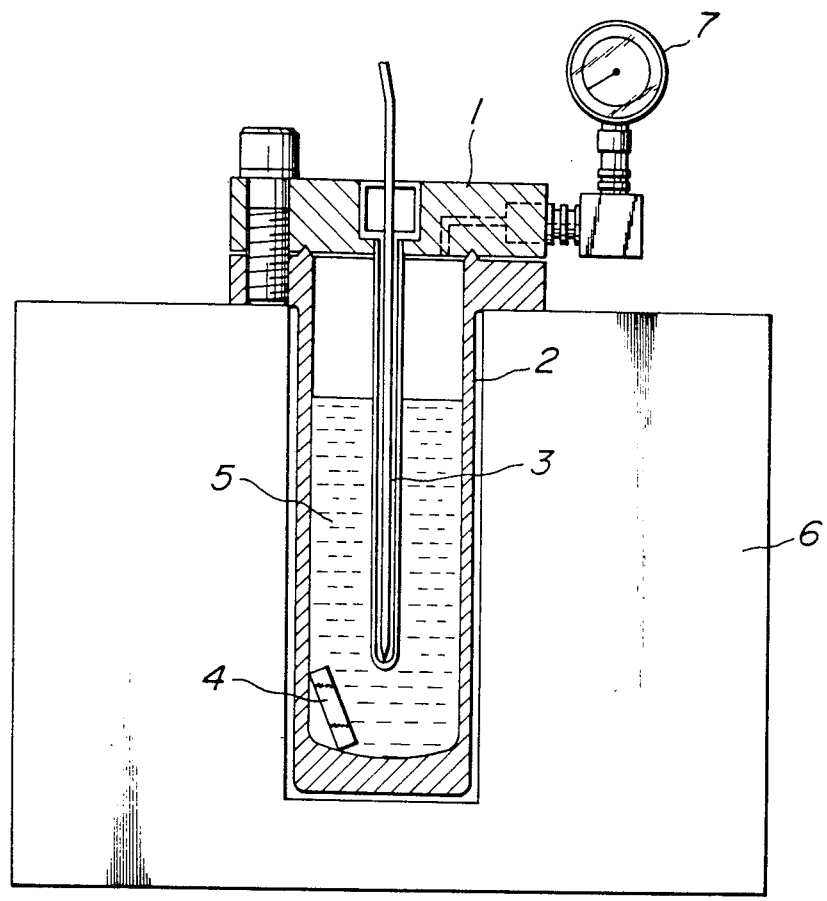

CERAMIC TESTING METHOD

BACKGROUND OF THE INVENTION

1. Field of the Invention

This invention relates to a ceramic testing method, and more particularly to a method of testing ceramics containing tetragonal zirconia.

2. Description of the Prior Art

Ceramics containing tetragonal zirconia has been extensively studied as a material for high-temperature structures, cutting tools, and oxygen sensors, because of their high heat resistivity, high mechanical strength, and high toughness and its special properties of ionic conductivity at high temperatures.

Zirconia is stable in tetragonal crystal phase at high temperatures, while it is stable in monoclinic crystal phase at low temperatures, so that when it is subjected to a temperature change in excess of a certain range, phase transformation is caused in zirconia accompanied with a considerable change in its volume.

As well known to those skilled in the art, in producing ceramics containing zirconia, it is usually fired at a high temperatures, so that zirconia contained in the ceramics at high temperatures is in tetragonal phase. In the process of being cooled, the tetragonal phase of zirconia is transformed into monoclinic phase, and such transformation is accompanied with volumetric expansion which tends to form cracks therein and deteriorate the strength thereof.

To avoid this difficulty, it has been practiced to add oxides such as yttria and magnesia into zirconia or to control the microstructure of the sintered body, so as to maintain the tetragonal zirconia, which is stable at high temperatures, as a quasi-stable phase at low temperatures. Whereby, the transformation from tetragonal phase to monoclinic phase of crystal system is minimized, and the cracks due to such transformation are eliminated, so that strong ceramics containing zirconia can be produced. However, such quasi-stable tetragonal zirconia has a shortcoming in that, although the zirconia contained in the thus produced ceramics is prevented from being transformed into its monoclinic phase for a comparatively short period of time, it is gradually transformed as time elapses, and deterioration such as occurrence of cracks and reduction in mechanical strength may result. Efforts have been made to eliminate materials which are liable to such deterioration.

With conventional ceramic testing methods, it has been very difficult to foresee possible deterioration of materials. According to a conventional practice, the subject ceramics or materials are exposed to specific use conditions for a specific period of time, and then they are tested to determine the occurrence of deterioration. Such conventional test method, which is a kind of durability test, has a shortcoming in that it is costly and it requires long test time. Thus, with the conventional ceramic testing methods, development of highly reliable ceramics containing zirconia has been difficult due to the lack of quickly obtainable test result, and users have to do without guarantee of the reliability of such ceramic products.

SUMMARY OF THE INVENTION

Therefore, an object of the present invention is to obviate the above-mentioned shortcoming of the prior art by providing an improved ceramic testing method which enables quick determination of the reliability of ceramics containing tetragonal zirconia.

A ceramic testing method according to the present invention is characterized in that a specimen of ceramics containing tetragonal zirconia is heated in water or in water vapor atmosphere for a predetermined period of time.

Preferably, the water vapor atmosphere contains not less than 0.08 g/l of water, more preferably not less than 2.5 g/l of water. The ceramics to be tested preferably contains not less than 5% by weight of zirconia, more preferably not less than 50% by weight of zirconia. The maximum limit of the zirconia content allowable in the ceramic testing method of the invention is 100% by weight. The preferable temperature range for heating the specimen is 50°–1,250° C., more preferably 150°–500° C.

As described above, when a ceramics body containing zirconia is fired at a high temperature, a fired body containing tetragonal zirconia is obtained. As the fired body is cooled, transformation from tetragonal phase to monoclinic phase occurs at a temperature below the thermodynamic equilibrium temperature between the tetragonal and monoclinic crystalline systems. This transformation tends to cause cracks and deterioration of properties such as mechanical strength and electric characteristics. The probability of occurrence of such transformation of zirconia from its tetragonal phase to its monoclinic phase and the probability of deterioration of the ceramics containing tetragonal zirconia depend on various factors, and the actual degree of deterioration after use varies considerably depending on the materials and the manner of use.

The inventors found that a very important factor, which rules the deterioration of ceramics containing tetragonal zirconia due to the zirconia transformation from tetragonal phase to monoclinic phase, is the amount of water contained in the atmosphere, in addition to the conventionally known major factors affecting such deterioration, i.e., the kinds and amounts of additives dissolved in solid phase in the zirconia, magnitudes and amounts of tetragonal zirconia crystal grains, temperatures held, and durations of holding such temperatures. The present invention is based on this finding of the effect of water on the deterioration in question.

The rate of deterioration of ceramics containing tetragonal zirconia increases with the increase of water content in the atmosphere. The details of the mechanism in which water accelerates the deterioration of ceramics containing tetragonal zirconia are not clear yet, but it appears that water reduces the surface energy of the monoclinic crystal so as to facilitate generation of crystal nuclei for the transformation.

The effect of water to accelerate deterioration is recognized only in that ceramics which contains tetragonal zirconia in a temperature range where the tetragonal crystal becomes quasi-stable below the equilibrium temperature between the tetragonal and monoclinic phases. In the case of ceramics having no transformation, such as stabilized zirconia and alumina, the above-mentioned effect of water to accelerate deterioration is not recognized. Thus, water relates to the transformation of tetragonal zirconia into monoclinic zirconia. Especially, water has an effect of accelerating the deterioration of ceramics containing tetragonal zirconia.

To predict the nature of deterioration of ceramics containing tetragonal zirconia after actual use of it for a long period of time, one can put the ceramics in an atmosphere containing more water than that in the actual atmosphere wherein it is used for a certain period of time while keeping it at a temperature suitable for causing the transformation, and then can measure the degree of deterioration. In practice, for instance, a specimen and water are sealed in a closed vessel, and the vessel is heated from the outside and the vessel temperature is controlled at a suitable level, so as to keep the specimen in water or in water vapor atmosphere for a predetermined period of time.

The content of water in the atmosphere surrounding the specimen can be determined from the temperature held, the pressure held, the weight of water added, and the inner volume of the vessel, while considering the equilibrium of water. In addition to pure water, if other substances such as alcohol and water glass are added, the content of water in the atmosphere during the test can be determined by separate measurements preceding the test concerning the water content in the atmosphere for different temperatures and pressures under similar conditions. It is also possible to determine the water content directly by applying Karl Fischer titration or other analytical process to a sample taken from the actual test atmosphere.

The vessel to which the specimen and water are to be added need not always be sealed. The specimen may be placed in an open vessel and then exposed to water or water vapor. In this case, the water content of the atmosphere can be determined by regular measurement of humidity of the atmosphere. The specimen of the ceramics can be a ceramic article as used or can be a piece of ceramics cut off from such article.

After exposing to the atmosphere containing water vapor, the specimen is cooled, and then the degree of deterioration of the specimen is determined by a suitable method; such as a visual inspection method for checking the presence of cracks on the specimen surface, a dye-absorption test method for checking the presence of cracks by suitable dye such as red ink, a crack detecting method using a supersonic defect detector or an x-ray penetration defect detector, a method of measuring the amount of transformation from tetragonal phase to monoclinic phase by measurement of thermal expansion hysteresis or the x-ray diffraction measurement, a test method using the measurement of strength, a test method using the measurement of thermal shock resistance, a test method using the measurement of shape, or an electrical test method using the measurement of ionic conductivity.

The reasons for numerical limitations of conditions in the method of the invention will be described now. The water content in the atmosphere is preferably not less than 0.08 g/l, because the water content of saturated steam at 50° C. is about 0.08 g/l, so that if the water content in the atmosphere is less than 0.08 g/l, such atmosphere with a low humidity is comparable with the regular atmosphere in which the ceramics containing tetragonal zirconia is actually used, and the desired effect of accelerating deterioration cannot be expected. If the water content in the atmosphere is in excess of 2.5 g/l, the resistivity against deterioration of the ceramics containing tetragonal zirconia can be evaluated in a short period of time. The preferable content of zirconia in the ceramics is not less than 5% by weight, because if the content of zirconia in the ceramics is less than 5% by weight, any substantial improvement of the strength and toughness cannot be achieved. Not less than 50% by weight of zirconia is preferable, because when such amount or zirconia is contained, various properties inherent to zirconia can be revealed in the ceramics such as heat insulation, ionic conductivity, and resistivity against chemicals. The preferable heating temperature is 50°–1,250° C., because the deterioration usually occurs in this temperature range. The more preferable temperature range is 150°–500° C., because the rate of deterioration is very high in this temperature range.

BRIEF DESCRIPTION OF THE DRAWING

For a better understanding of the invention, reference is made to the accompanying drawing, in which:

The single drawing is a schematic sectional view of a measuring system which is suitable for carrying out the ceramic testing method according to the present invention.

In the single drawing, 1 is an autoclave, 2 is a vacuum casing, 3 is a thermocouple, 4 is a specimen, 5 is water, 6 is a heater, and 7 is a manometer.

DESCRIPTION OF THE PREFERRED EMBODIMENT

The single drawing shows an autoclave 1 for testing strength of ceramics by a method according to present invention. The autoclave 1 has a vacuum casing 2 carrying a thermocouple 3, and a specimen 4 of the ceramics to be tested is placed in the vacuum vessel 2 together with water 5. A heater 6 surrounds the vacuum vessel 2, and a manometer 7 measures the pressure in the vacuum vessel 2.

The invention will be described in further detail now by referring to Examples.

Example 1

Starting powder material was prepared by weighing 91.8% by weight of zirconia on the market and 8.2% by weight of yttria on the market, mixing and pulverizing them in a ball mill for 50 hours, and drying the mixture thus pulverized. The starting powder material was shaped into plates, each plate having a width of 60 mm, a length of 60 mm, and a thickness of 6 mm, and a static hydraulic pressure of 1,000 kg/cm$^2$ was applied thereto. Three groups of the thus shaped plates were fired at different temperatures for three hours; a first group at 1,400° C., a second group at 1,500° C., and a third group at 1,600° C.

Strength test specimens, each having a cross section of 3×4 mm and a length of 40 mm, were prepared from the thus fired plates by using a diamond cutter and a diamond grindstone in accordance with the stipulations of Japanese Industrial Standard (JIS) R 1601 "Test Method of Bending Strength of Fine Ceramics".

Disk specimens, each having a diameter of 20 mm and a thickness of 3 mm, for x-ray diffraction measurement were prepared, and their surfaces were finished by buffing so as to provide a surface roughness of less than 0.8 S as stipulated in JIS B 0601.

The strength test specimens were placed in the autoclave as shown in the accompanying drawing, so as to process them at certain temperatures for predetermined periods of time. For reference, the specimens were placed in an electric furnace for effecting aging treatment in air at certain temperatures for predetermined periods of time. Both before and after such processes and treatments, various tests were carried out; i.e., visual inspections for checking cracks, dye-absorption tests for checking surface fine cracks, and strength tests.

The strength tests were carried out by the four-point bending method as stipulated in JIS R 1601.

The x-ray diffraction measurements were taken on the above-mentioned disk specimens by using a copper (Cu) bulb x-ray diffraction device under the conditions of a bulb voltage of 50 kV, a bulb current of 80 mA, and a scanning speed of 0.25°/min. The presence of tetragonal zirconia was checked by using the tetragonal zirconia ($ZrO_2$) peaks (200), (002), (004), and (220).

The result of the tests is shown in Table 1. In the table, under the heading of "dye-absorption test", the symbol A represents no exudation, the symbol B represents slight exudation, and the symbol C represent considerable exudation.

In the case of the zirconia porcelain used in the test of this example, accelerated aging was noticed when being heated at about 250° C. under the presence of water, and the degree of the accelerated aging increased with the rise of the firing temperature. As shown in Table 1, when the zirconia porcelain specimens were heated at about 250° C. in air having a regular humidity with a water content of 0.005–0.2 g/l, the aging occurred only after heating over a long period in the order of 1,000 hours. If the same specimens were heated in an atmosphere with a high water content, similar aging could result in a very short period of time.

Example 2

Specimens of various ceramics containing tetragonal zirconia were subjected to temperature cycle tests in air by raising and reducing the temperature at a rate of 200° C./hr in a range of 100° C. to 1,000° C.

Similar specimens were heated at certain temperatures for a predetermined period of time in an atmosphere with a high water content, and then dye-absorption tests were applied to the thus heated specimens.

The result is shown in Table 2. For reference, result of tests outside the scope of the invention is also shown in the table.

The test result proved that the method of the invention was effective in quickly detecting those defective ceramics containing tetragonal zirconia which would be easily aged.

The test result on reference specimens of stabilized zirconia ceramics and alumina ceramics showed that no aging was caused in those ceramics which did not contain tetragonal zirconia even after heating in an atmosphere with a high water content. Thus, the method of the present invention is clearly different from regular water corrosion tests, because the method of the invention is particularly useful in testing the aging of ceramics containing tetragonal zirconia.

TABLE 1

| Test No. | Specimen Type of ceramics | Composition (% by Wt) | Tetragonal zirconia | Atmosphere | Water content in atmosphere (g/l) | Pressure (Atm) | Temperature (°C.) | Time (Hr) | Strength (MPa) | Cracks | Dye-absorption test*** |
|---|---|---|---|---|---|---|---|---|---|---|---|
| 1 | zirconia | | | in water** | 799 | 39 | 250 | 10 | 820 | none | A |
| (2) | ceramics | | | | none | | | | 810 | none | A |
| (3) | A* | | | in air | 0.005–0.02 | 1 | 250 | 1,000 | 800 | none | A |
| 4 | | | | in water** | 958 | 1 | 100 | 10 | 840 | none | A |
| 5 | | | | " | 917 | 5 | 150 | 10 | 720 | none | B |
| 6 | | | | " | 865 | 15 | 200 | 10 | 340 | none | B |
| 7 | | | | " | 799 | 39 | 250 | 1 | 530 | none | B |
| 8 | | | | " | 799 | 39 | 250 | 10 | 210 | exist | C |
| 9 | | | | " | 799 | 39 | 250 | 100 | 0 | exist | C |
| 10 | zirconia | $ZrO_2$: 91.8 | | in steam** | 20.0 | 39 | 250 | 10 | 470 | exist | C |
| 11 | ceramics | | contained | in water** | 712 | 85 | 300 | 10 | 230 | exist | C |
| 12 | B* | $Y_2O_3$: 8.2 | | " | 572 | 163 | 350 | 10 | 600 | exist | B |
| (13) | | | | | none | | | | 830 | none | A |
| (14) | | | | in air | 0.005–0.02 | 1 | 100 | 1,000 | 820 | none | A |
| (15) | | | | in air | 0.005–0.02 | 1 | 250 | 100 | 830 | none | A |
| (16) | | | | in air | 0.005–0.02 | 1 | 250 | 1,000 | 210 | exist | C |
| (17) | | | | in air | 0.005–0.02 | 1 | 500 | 1,000 | 790 | none | A |
| (18) | | | | in air | 0.005–0.02 | 1 | 800 | 1,000 | 850 | none | A |
| 19 | zirconia | | | in water** | 799 | 39 | 250 | 10 | 0 | exist | C |
| (20) | ceramics | | | | none | | | | 780 | none | A |
| (21) | C* | | | in air | 0.005–0.02 | 1 | 250 | 1,000 | 540 | exist | C |

Notes:
1. Test Nos. in bracket show the result outside the scope of invention.
2. *Zirconia ceramics A, B, and C were fired at 1,400° C., 1500° C., and 1,600° C., respectively.
**In water in autoclave, and in steam in autoclave.
***In dye-absorption test, symbols A, B, and C represent no, slight, and much absorption, respectively.

TABLE 2

| Test No. | Specimen Type of ceramics | Composition (% by Wt) | Tetragonal zirconia | Atmosphere | Water content in atmosphere (g/l) | Pressure (Atm) | Temperature (°C.) | Time (Hr) | Dye-absorption test** |
|---|---|---|---|---|---|---|---|---|---|
| 1 | zirconia | $Zr_2O_3$: 93.2 | contained | in steam* | 20.0 | 39 | 250 | 1 | C |
| 2 | ceramics | $Y_2O_3$: 5.0 | contained | in water* | 799 | 39 | 250 | 1 | C |
| (3) | D | $Al_2O_3$: 1.8 | contained | in air | 0.005–0.02 | 1 | note 3 | 100 | A |
| (4) | | | contained | in air | 0.005–0.02 | 1 | note 3 | 1,000 | C |
| 5 | zirconia | $ZrO_2$: 93.1 | contained | in water* | 799 | 39 | 250 | 10 | A |
| (6) | ceramics | $Y_2O_3$: 4.8 | contained | in air | 0.005–0.02 | 1 | note 3 | 100 | A |
| (7) | E | $SiO_2$: 2.1 | contained | in air | 0.005–0.02 | 1 | note 3 | 1,000 | A |
| 8 | | | contained | in steam | 0.256 | 1 | 600 | 100 | C |
| 9 | zirconia | $ZrO_2$: 96.9 | contained | in water* | 799 | 39 | 250 | 10 | C |
| (10) | ceramics | MgO: 3.1 | contained | in air | 0.005–0.02 | 1 | note 3 | 100 | A |
| (11) | F | | contained | in air | 0.005–0.02 | 1 | note 3 | 1,000 | C |

TABLE 2-continued

| | Specimen | | | Aging test | | | | | Dye-absorption test** |
|---|---|---|---|---|---|---|---|---|---|
| Test No. | Type of ceramics | Composition (% by Wt) | Tetragonal zirconia | Atmosphere | Water content in atmosphere (g/l) | Pressure (Atm) | Temperature (°C.) | Time (Hr) | |
| 12 | alumina ceramics | $Al_2O_3$: 92.5 $ZrO_2$: 7.5 | contained | in water* | 799 | 39 | 250 | 10 | C |
| (13) | | | contained | in air | 0.005–0.02 | 1 | note 3 | 100 | A |
| (14) | | | contained | in air | 0.005–0.02 | 1 | note 3 | 1,000 | C |
| (15) | stabilized zirconia ceramics | $ZrO_2$: 86.4 $Y_2O_3$: 13.6 | none | none | | none | | | A |
| (16) | | | none | in air | 0.005–0.02 | 1 | note 3 | 1,000 | A |
| (17) | | | none | in water* | 799 | 39 | 250 | 10 | A |
| (18) | alumina ceramics | $Al_2O_3$: 100 | none | none | | none | | | A |
| (19) | | | none | in air | 0.005–0.02 | 1 | note 3 | 1,000 | A |
| (20) | | | none | in water* | 799 | 39 | 250 | 10 | A |

Notes:
1. Test Nos. in bracket show the result outside the scope of invention.
2. *In water in autoclave, and in steam autoclave.
**In dye-absorption test, symbols A, B, and C represent no, slight, and much absorption, respectively.
3. Temperature in aging test was cyclically changed between 100° C. and 1,000° C.

As described in detail in the foregoing, the reliability of ceramics containing tetragonal zirconia can be determined in a very short period of time. Such ceramics containing tetragonal zirconia has a high resistivities against mechanical and thermal stresses; namely, regular thermal stress, thermal shock stress, repeated stress, and repeated thermal stress. Examples of the use of such ceramics containing tetragonal zirconia include engine cylinder liners, piston caps, cylinder heads, valves, valve guides, exhaust ports, rocker arms, auxiliary combustion chambers, tappets, and oxygen sensors. Besides, the ceramics containing tetragonal zirconia is also useful as material for acid-resistive pump and other parts exposed to acids, alkalis, and various chemicals. The ceramics containing tetragonal zirconia is also used as material for cutting tools, such as surgical knives, scissors, regular knives, and the like.

The ceramic testing method according to the present invention facilitates research and development of ceramics containing tetragonal zirconia which ensures high durability and high reliability. With the method of the invention, tests for quality control of production can be effected quickly, and the durability of the products may be guaranteed based on such tests.

Although the invention has been described with a certain degree of particularity, it is understood that the present disclosure has been made only by way of example, and that numerous changes in details of steps and the combination and arrangement of parts may be resorted to without departing from the scope of the invention as hereinafter claimed.

What is claimed is:

1. A ceramic testing method comprising the steps of heating a ceramic specimen containing tetragonal zirconia in water or a water vapor atmosphere containing not less than 2.5 g/l of water at a temperature in a range of 150°–1,250° C., for a time sufficient to result in deterioration of any non-stabilized zirconia that is present in said ceramic specimen, and measuring the degree of deterioration of the ceramic specimen to evaluate long term durability and reliability of the ceramic specimen.

2. A ceramic testing method comprising the steps of heating a ceramic specimen containing not less than 5% by weight of tetragonal zirconia in water or a water vapor atmosphere containing not less than 2.5 g/l of water at a temperature in a range of 150°–500° C. for a period of time between one hour and one hundred hours sufficient to result in deterioration of any non-stabilized zirconia that is present in said ceramic specimen, and measuring the degree of deterioration of the ceramic specimen to evaluate long term durability and reliability of the ceramic specimen.

3. A ceramic testing method as set forth in claim 2, wherein said measuring of the ceramic specimen comprises a process selected from the group consisting of visual inspection for surface cracks, dye-absorption crack testing, supersonic crack detecting, X-ray penetration detecting, thermal expansion measurement, X-ray diffraction measurement, strength measurement, thermal shock resistance measurement, shape measurement and ionic conductivity measurement.

4. A ceramic testing method as set forth in claim 1, wherein said ceramic specimen contains not less than 5% by weight of zirconia.

5. A ceramic testing method as set forth in claim 1, wherein said ceramic specimen contains not less than 50% by weight of zirconia.

6. A ceramic testing method as set forth in claim 1, wherein said measuring of the ceramic specimen comprises a process selected from the group consisting of visual inspection for surface cracks, dye-absorption crack testing, supersonic crack detecting, X-ray penetration detecting, thermal expansion measurement, X-ray diffraction measurement, strength measurement, thermal shock resistance measurement, shape measurement and ionic conductivity measurement.

7. A ceramic testing method as set forth in claim 1, wherein said heating is effected at a temperature in a range of 150°–500° C.

8. A ceramic testing method as set forth in claim 1, wherein said ceramic specimen is resistive against mechanical and thermal stresses including regular thermal stress, thermal shock stress, repeated stress, and repeated thermal stress.

9. A ceramic testing method as set forth in claim 1, wherein said ceramic specimen is resistive against acidic corrosion.

10. A ceramic testing method as set forth in claim 1, wherein said ceramic specimen is resistive against alkali corrosion.

* * * * *